United States Patent
Tiesma et al.

(10) Patent No.: US 8,409,109 B2
(45) Date of Patent: Apr. 2, 2013

(54) RECTAL PROBE WITH DISPOSABLE BALLOON ASSEMBLY

(75) Inventors: Scott R. Tiesma, New Hope, MN (US); David A. Montecalvo, Orono, MN (US)

(73) Assignee: Urologix, Inc., Plymouth, MN (US)

( * ) Notice: Subject to any disclaimer, the term of this patent is extended or adjusted under 35 U.S.C. 154(b) by 1776 days.

(21) Appl. No.: 11/091,107

(22) Filed: Mar. 28, 2005

(65) Prior Publication Data

US 2005/0222517 A1 Oct. 6, 2005

Related U.S. Application Data

(60) Provisional application No. 60/558,746, filed on Apr. 1, 2004.

(51) Int. Cl.
*A61B 5/00* (2006.01)
*A61B 1/04* (2006.01)
*A61B 1/00* (2006.01)
*A61M 29/00* (2006.01)

(52) U.S. Cl. ........ 600/549; 600/115; 600/116; 600/121; 606/192; 606/197; 606/198

(58) Field of Classification Search .......... 600/115–116, 600/549; 604/101.01, 101.02, 912, 915; 606/192, 193, 195–198; 383/3, 38–40
See application file for complete search history.

(56) References Cited

U.S. PATENT DOCUMENTS

| | | | | |
|---|---|---|---|---|
| 3,162,190 A | * | 12/1964 | Del Gizzo | 600/123 |
| 3,496,931 A | * | 2/1970 | Pilling | 600/128 |
| 4,054,057 A | | 10/1977 | Kluge | |
| 4,128,007 A | | 12/1978 | Ulin | |
| 4,883,465 A | * | 11/1989 | Brennan | 604/96.01 |
| 5,335,669 A | | 8/1994 | Tihon et al. | |
| 5,342,301 A | * | 8/1994 | Saab | 604/103.13 |
| 5,501,667 A | * | 3/1996 | Verduin, Jr. | 604/101.01 |
| 5,792,070 A | | 8/1998 | Kauphusman et al. | |
| 5,911,700 A | * | 6/1999 | Mozsary et al. | 604/22 |
| 5,944,734 A | * | 8/1999 | Hermann et al. | 606/192 |
| 6,096,065 A | * | 8/2000 | Crowley | 607/88 |
| 6,348,039 B1 | | 2/2002 | Flachman et al. | |
| 6,666,828 B2 | * | 12/2003 | Greco et al. | 600/561 |
| 2002/0091405 A1 | * | 7/2002 | Kieturakis et al. | 606/190 |
| 2005/0177025 A1 | * | 8/2005 | Jaker et al. | 600/121 |

* cited by examiner

*Primary Examiner* — Max Hindenburg
*Assistant Examiner* — John Pani
(74) *Attorney, Agent, or Firm* — Dicke, Billig & Czaja, PLLC (57) ABSTRACT

A reusable temperature sensing probe assembly comprises a temperature sensor strip extending from one end of a handle. The temperature sensor strip carries at least one temperature sensor for measuring temperature within a body cavity of a person, such as the rectum. The handle/temperature sensor strip is reversibly positionable within a unitary balloon/sleeve assembly comprised of a balloon portion and a sleeve portion. The balloon portion is comprised of a first interior space configured to hold the temperature sensor stip and a second interior space separate from the first interior space that is configured for inflation. An inflation tube has one portion sealed within the second interior space of the balloon portion and a second portion which extends through the sleeve portion for connection to a fluid source.

18 Claims, 7 Drawing Sheets

RECTAL PROBE WITH DISPOSABLE BALLOON ASSEMBLY

CROSS-REFERENCE TO RELATED APPLICATION(S)

This application claims the benefit of Provisional Application No. 60/558,746 filed Apr. 1, 2004 for RECTAL PROBE WITH DISPOSABLE BALLOON ASSEMBLY".

BACKGROUND OF THE INVENTION

The present invention relates to a temperature sensing probe for sensing rectal temperature of a patient. In particular, the present invention relates to a temperature sensing probe comprising a reusable handle and sensor array with a disposable balloon/sleeve assembly.

The prostate gland is a complex, chestnut-shaped organ which encircles the urethra immediately below the bladder and lies immediately adjacent the rectum. This relatively small organ, which is the most frequently diseased of all internal organs, is the site of a common affliction among older men, benign prostatic hyperplasia (BPH), as well as a more serious affliction, cancer. BPH is a non-malignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

A fairly recent treatment method for BPH involves microwave thermal therapy, in which microwave energy is employed to elevate the temperature of tissue surrounding the prostatic urethra above about 45° C., thereby thermally damaging the tumorous BPH tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a radiation pattern which encompasses and necroses the tumorous prostatic tissue. The necrosed intraprostatic tissue is subsequently reabsorbed by the body, thereby relieving an individual from the symptoms of BPH.

One type of thermal therapy treatment of BPH is transurethral microwave thermotherapy. This method of treatment positions a Foley-type catheter containing a microwave antenna within the urethra adjacent to the prostate gland. The microwave antenna is energized to heat a selected volume of tumorous prostatic tissue surrounding the urethra to about 45° C. for a time sufficient to necrose the selected volume of tissue.

Due to the relatively close proximity of the rectum to the urethra, it is critically important in the course of transurethral microwave thermotherapy that the temperature of the rectum is maintained below a threshold temperature. Rectal temperatures greater than the threshold may cause damage to the rectum.

Typically, the temperature of rectal tissue adjacent the prostate is measured and monitored with a rectal temperature sensing probe. The probe supports one or more temperature sensing elements against a wall of the rectum adjacent to the prostate to provide the physician with essential information for controlling the location and degree of heat induced in the prostate. In providing a rectal probe to measure the temperature of rectal tissue adjacent the prostate, it is desirable to maintain the position of a temperature sensing device supported by the probe directly adjacent to the rectal wall to provide optimally accurate temperature readings. There is a continuing need for an improved rectal temperature sensing probe.

BRIEF SUMMARY OF THE INVENTION

The present invention is a temperature sensing probe assembly comprising a reusable temperature sensor/handle assembly and a balloon/sleeve assembly. The temperature sensor/handle assembly is comprised of a handle having a length, a width, a first end and a second end, and a temperature sensor strip carried by the handle and extending from the first end of the handle. The temperature sensor strip comprises a temperature sensor spaced from the first end. The temperature sensor is configured for connection to a thermometry device. The balloon/sleeve assembly comprises opposing first and second polymeric layers configured to define a balloon portion and a sleeve portion. The balloon portion further comprising a first interior space in communication with an interior space of the sleeve portion, and a second interior space isolated from the first interior space and the interior space of the sleeve portion. A first tube portion of an inflation tube is sealingly connected within the second interior space of the balloon portion and is configured with an inflation port. A second tube portion of the inflation tube extends through the sleeve portion and is configured for connection to a fluid source. The handle is reversibly positionable within the sleeve portion and the temperature sensor strip is reversibly positionable within the first interior space of the balloon portion.

While the above-identified drawing figures set forth preferred embodiments of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention. It should be specifically noted that the figures have not been drawn to scale, as it has been necessary to enlarge certain portions for clarity.

DETAILED DESCRIPTION

Figure 1:
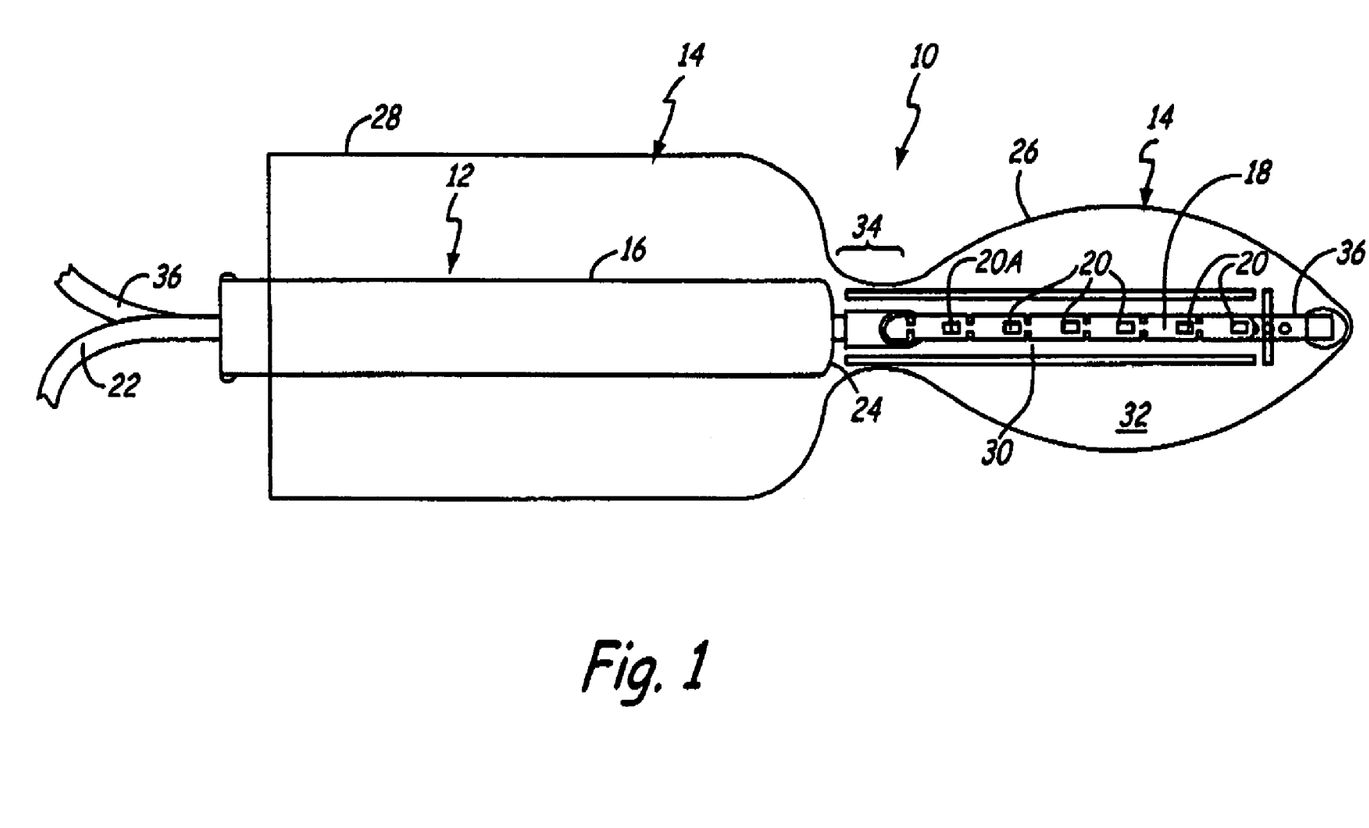
FIG. 1 is a top view of the rectal temperature sensing probe of the present invention.

FIG. 1 is a top view of the rectal temperature sensing probe 10 of the present invention. As shown in FIG. 1, probe 10 is generally comprised of a probe handle 12 and a balloon/sleeve assembly 14. The probe handle 12 includes a handle body 16 and a temperature sensor array 18 which carries a plurality of longitudinally spaced temperature sensors 20. In one embodiment, handle 16 is preferably formed of silicone in a molding process that captures a sensor cable 22, which is electrically connected to sensor array 18. Handle body 16 has a length of about 6.0 inches to about 6.5 inches and a nominal diameter of about 0.5 inches.

Temperature sensor array 18 is comprised of the plurality of temperature sensors 20 bonded to a flexible circuit which is housed within a protective strip. A suitable temperature sensor array is fully described in U.S. Pat. No. 5,792,070, which is incorporated herein by reference. In one embodiment, temperature sensor array 18 extends from a proximal end 24 of handle body 16, with temperature sensor 20A positioned approximately 1.75 inches to about 2.15 inches from proximal end 24. Temperature sensor array 18 has a length extending from proximal end 24 of handle body 16 of about 4.4 inches to about 4.6 inches. Temperature sensors 20 are oriented and spaced to sense a temperature of a wall of the rectum facing the prostate when probe 10 is properly positioned within the rectum of a patient undergoing a heat treatment of the prostate. Sensor cable 22 is configured for connection to a rectal thermometry unit to transmit a signal representative of the sensed wall temperature, as is fully described in the aforementioned U.S. Pat. No. 5,792,070.

The balloon/sleeve assembly 14 includes a balloon portion 26, which holds and carries temperature sensor array 18, and a sleeve portion 28, which enshrouds a portion of the handle body 16. The balloon/sleeve assembly 14 is designed to be a disposable unit that can be separated from the probe handle 12 after use of probe 10. The balloon portion 26 and sleeve portion 28 are formed from layers of a flexible, biocompatible polymer, such as polyurethane, in a manner to be more fully described. As shown in FIG. 1, the balloon portion 26 and sleeve portion 28 may be transparent to enable verification of a proper positioning of the temperature sensor array 18 within the balloon portion 26. The balloon portion 26 is formed with a central channel 30, which positions temperature sensor array 18 in a proper orientation relative to an outer surface 32 of the balloon portion 26. With temperature sensor array 18 properly positioned within channel 30, proximal end 24 of the probe handle 12 lies generally adjacent to a waist 34 of the balloon portion 26, which is a point of transition from the balloon portion 26 to the sleeve portion 28. Balloon portion 26 is dimensioned to fit within the rectum of a patient and engage the rectal wall when the balloon portion 26 is inflated, with the proximal end 24 of the probe handle 12 remaining external to the rectum. An inflation tube 36, which is in communication with a fluid source, extends along the probe handle 12 and into the balloon portion 26 to inflate the balloon portion 26. The sleeve portion 28 is sized to permit easy assembly and disassembly of the probe handle 12 from the balloon/sleeve assembly 14 and to cover the handle body 16 when probe 10 is in use.

Figure 2:
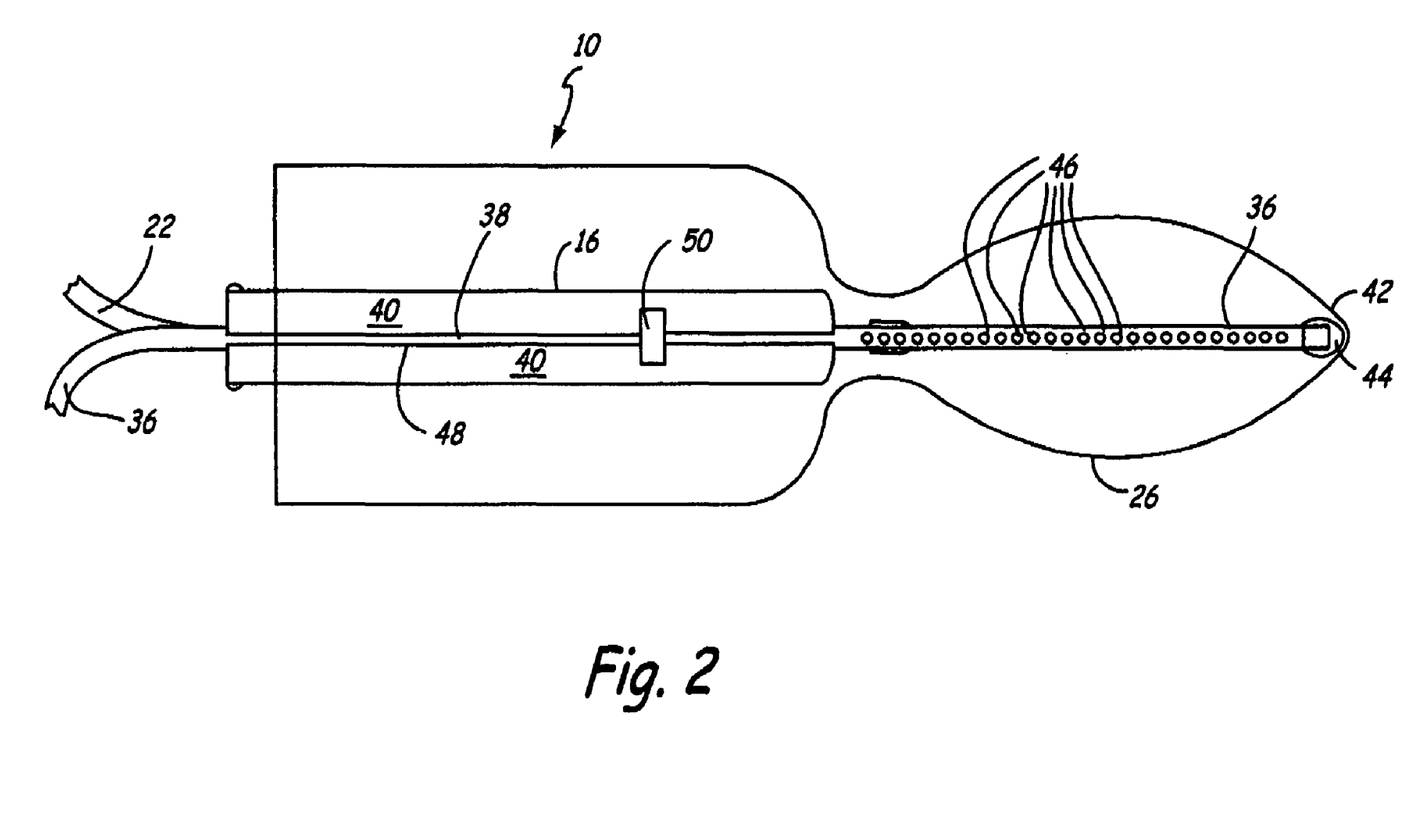
FIG. 2 is a bottom view of the rectal temperature sensing probe of FIG. 1.

FIG. 2 is a bottom view of the probe 10 of FIG. 1. As shown in FIG. 2, inflation tube 36 extends along the probe handle body 16 within a channel 38 formed relative to a bottom surface 40 of handle body 16. Inflation tube 36 extends to a tip 42 of balloon portion 26 and is configured with a bulbous end 44 in contact with the tip 42. The bulbous end 44 is fixed relative to the inflation tube 36 to provide a blunt surface in contact with an inner surface of balloon portion 26 for the safety of the patient in the event tip 42 contacts patient tissues. In one embodiment, inflation tube 36 is provided with a plurality of openings 46 within balloon portion 26 for the introduction of an inflation medium. The plurality of openings 46 are oriented on opposite sides of inflation tube 36 to provide flexibility in a preferred plane to allow for anterior rectal wall contact of temperature sensors 20 while maintaining column strength/flexural rigidity of inflation tube 36 sufficient for insertion of balloon portion 26 into the rectum. For increased flexibility at waist 34, the size of openings 46 at or near to waist 34 may increased or elongated.

Channel 38 of handle body 16 is dimensioned to secure inflation tube 36 relative to handle body 16 when inflation tube 36 is positioned therein. Accordingly, the elongated opening 48 of channel 38 has a width that is less than an outer diameter of inflation tube 36 when handle body 16 is unstressed. Owing to the flexible characteristics of the silicone material forming handle body 16, the opening 48, however, can yield sufficiently to permit the inflation tube 36 to be press fit into and removed from channel 38 with an application of sufficient force. In the absence of such force, the edges of opening 48 slightly overlap opposite sides of inflation tube 36 to retain inflation tube 36 within channel 38.

A longitudinal movement of inflation tube 36 relative to handle body 16 is prevented by means of a lock assembly formed between a key 50 secured to inflation tube 36 and a corresponding key slot formed in handle body 16 transverse to channel 38. The key slot in handle body 16 is positioned to align with the key 50 when temperature sensing array 18 is fully inserted into central channel 30. The lock assembly further ensures that a precise location of the temperature sensor array 18 within channel 30 (shown in FIG. 1) is maintained when probe 10 is in use.

Figure 3:
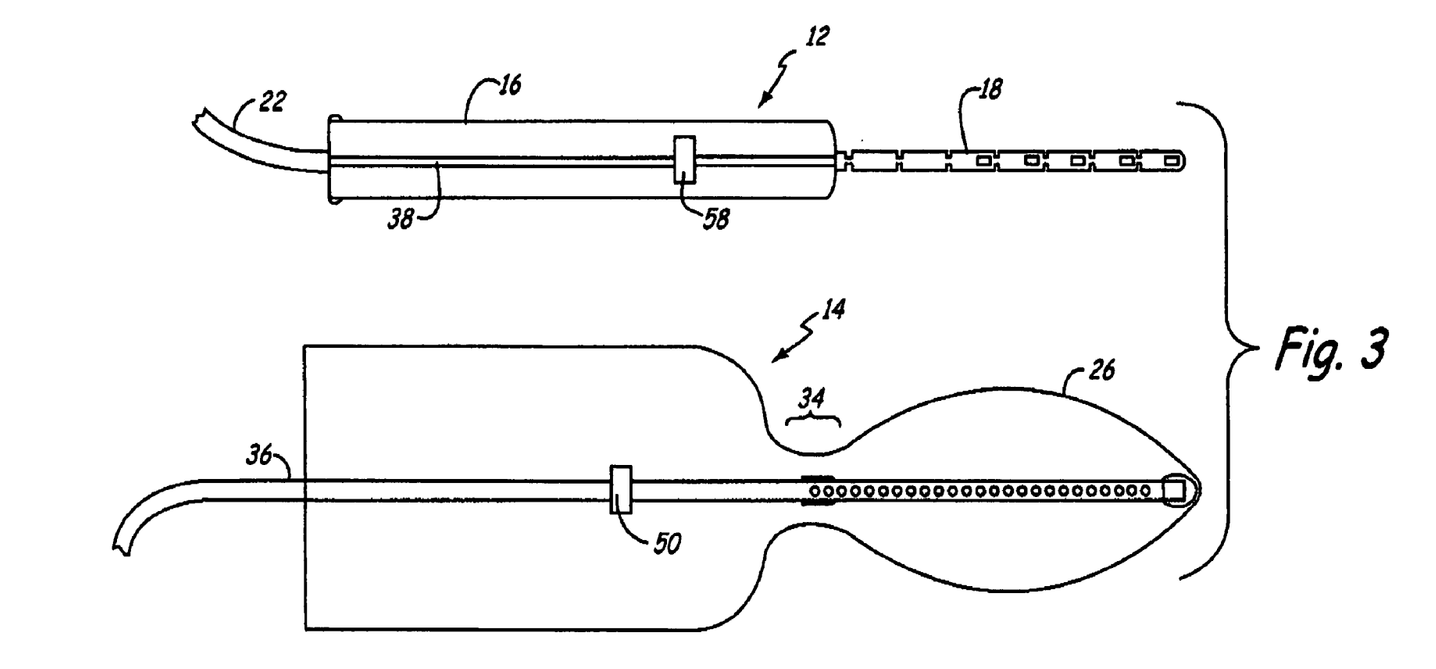
FIG. 3 is a bottom exploded view of the rectal temperature sensing probe of FIG. 1.
Figure 3A:
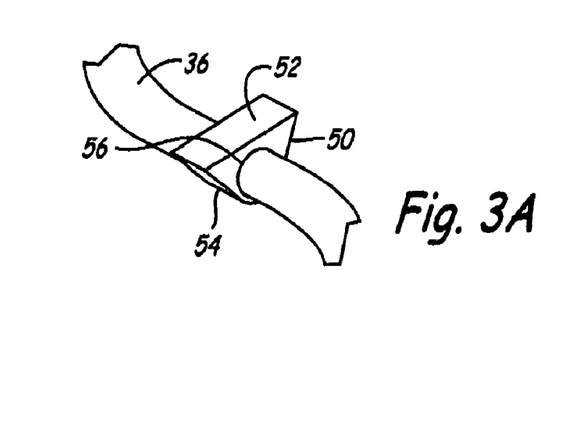

FIG. 3 is an exploded bottom view of probe 10 with the probe handle 12 separated from the balloon/sleeve assembly 14. As shown in FIG. 3, probe handle 12 is removable and separable from the balloon/sleeve assembly 14 to permit probe handle 12, i.e., and the temperature sensing array 18, to be reused with a new sterile balloon/sleeve assembly. The balloon/sleeve assembly 14 includes the inflation tube 36, which is connected between layers of the polymer material forming a balloon at the waist 34 of the balloon portion 26, as will be described in greater detail. As shown in FIG. 3A, the key 50 consists of a polymeric member having a flat edge portion 52, a curved edge portion 54 and a hole 56 passing through the member to permit key 50 to be slid into a position on inflation tube 36 corresponding to key slot 58 in handle body 16. Once key 50 is properly positioned, it is secured to inflation tube 36 by a suitable adhesive.

Figure 4:
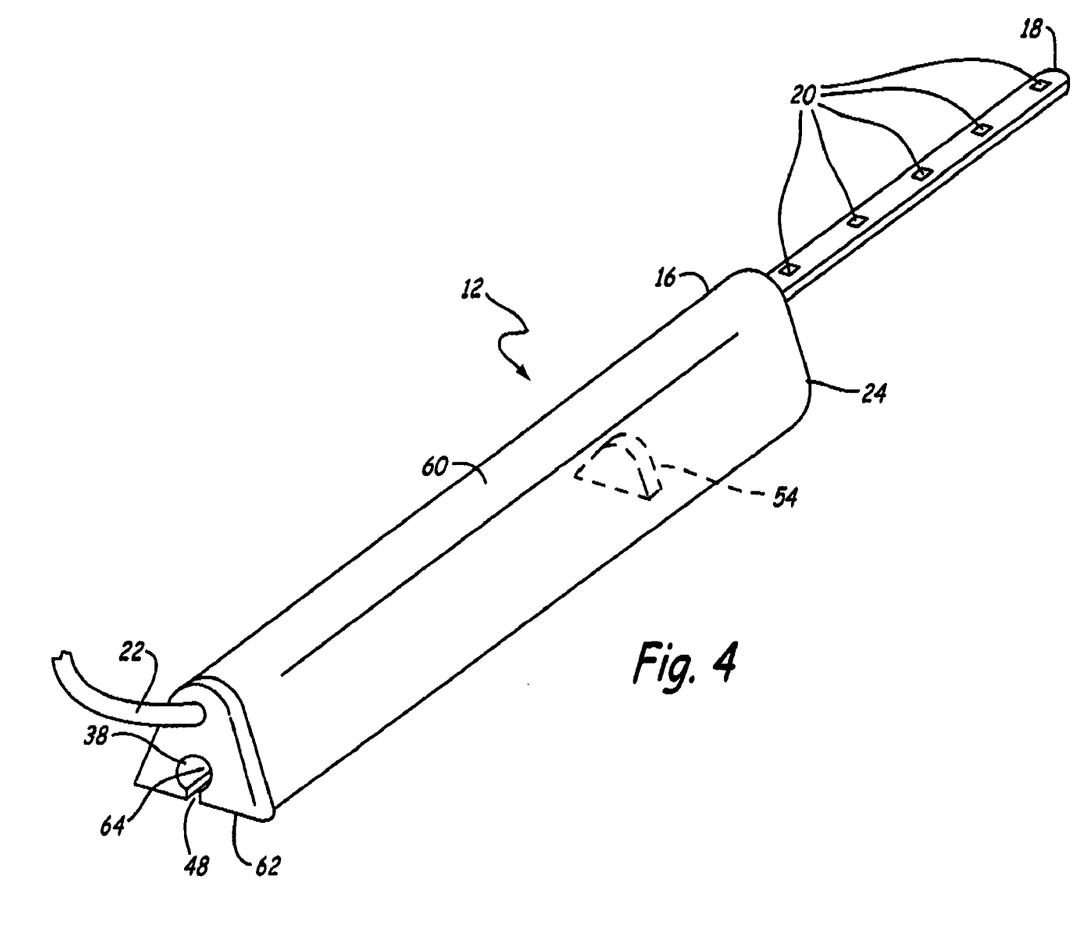
FIG. 4 is an enlarged perspective view of the reusable probe handle and temperature sensor array of the rectal temperature sensing probe of the present invention.

FIG. 4 is an enlarged perspective view of the probe handle 12, which shows that the handle body 16 is configured with a curved upper surface 60 and a flat lower surface 62. This configuration of handle body 16 facilitates a proper orientation of the probe 10 relative to a patient and monitoring of the proper orientation during use. In a proper orientation, the flat lower surface 62 of handle body 16 contacts a treatment surface occupied by a patient in the supine position and is maintained in contact with the treatment surface by the weight of the patient on the handle body 16. The configuration of handle body 16 thus inhibits any twisting of probe 10 by minor changes of position of the patient on the treatment surface.

As shown in FIG. 4, temperature sensor array 18 extends from the proximal end 24 of handle body 16 at an upper extent of handle body 16, and sensor cable 22 extends rearward of handle body 16 at a comparable upper extent. Temperature sensor array 18 is oriented in a plane that is generally parallel with the flat lower surface 62 of handle body 16, with sensors 20 oriented on the upper surface of the flexible circuit.

Channel 38 is generally centrally located relative to the flat lower surface 62. Channel 38 is defined by a curved inner wall 64 which has an inner diameter that approximates the outer diameter of the inflation tube 36 for retaining the inflation tube 36 in channel 38. The width of opening 48 of channel 38 is smaller than the inner diameter of inner wall 64, which aids in the retention of inflation tube 36 within channel 38. As shown in phantom, the key slot 54 is dimensioned and configured complimentary to key 50 to form a friction fit with key 50 when it is position within key slot 54.

Figure 5:
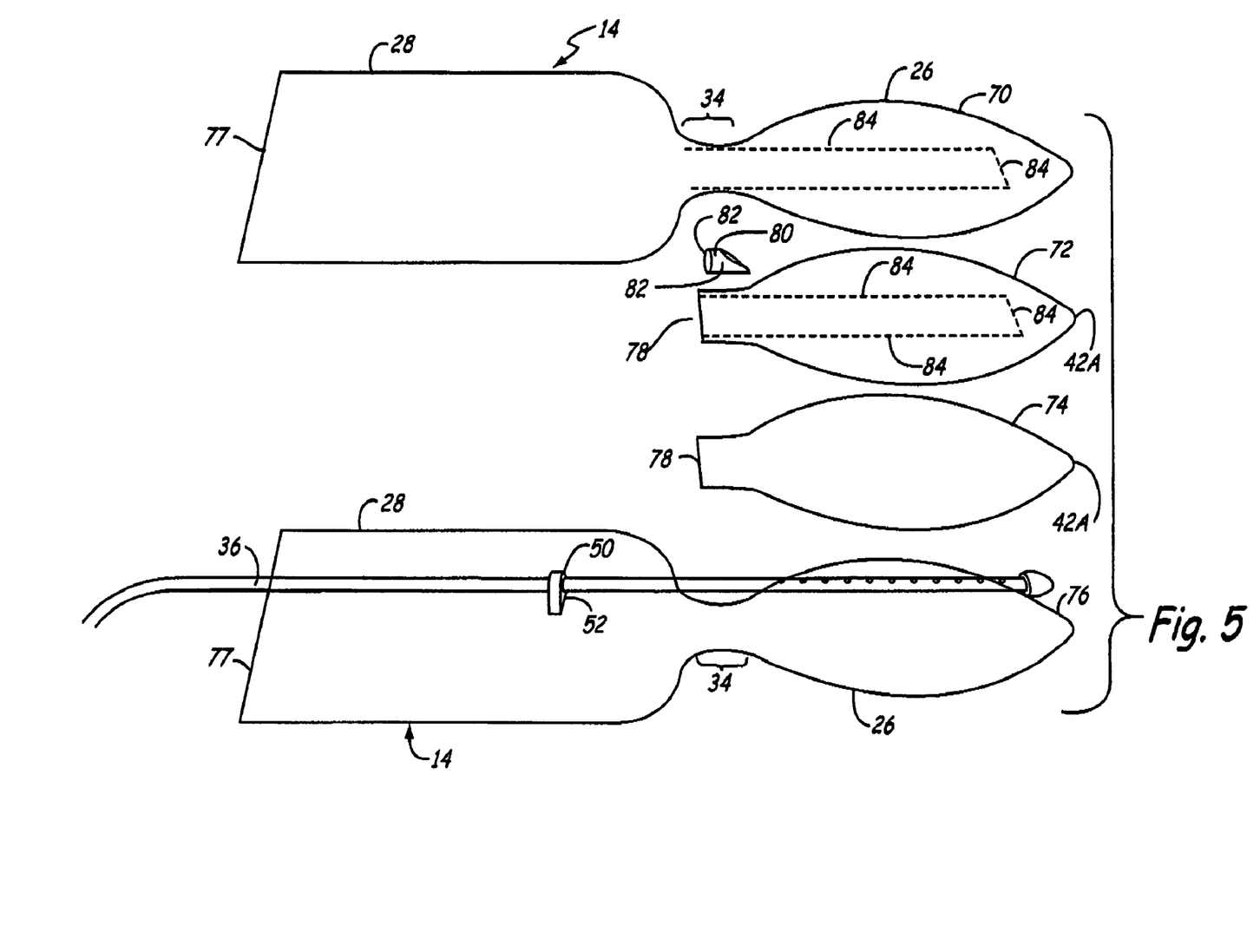
FIG. 5 is an exploded perspective view of the single use balloon/sleeve assembly of the rectal temperature sensing probe of the present invention.

FIG. 5 is an exploded view of the balloon/sleeve assembly 14. As shown in FIG. 5, in one embodiment, the balloon/sleeve assembly 14 is comprised of a plurality of overlying and interconnected layers 70, 72, 74 and 76 which are connected together along a common peripheral edge such as by heat welding. Layers 70 and 76 are each a unitary layer of polymer that defines the top and bottom layers, respectively, of balloon portion 26 and the sleeve portion 28 of the balloon/sleeve assembly 14. Edge portion 77 of layers 70 and 76 remain unconnected for inserting and removing probe handle 12 from the balloon/sleeve assembly 14. Layers 72 and 74 are also each a unitary layer of polymer that is a postage stamp of balloon portion 26, extending from a first end 42A to an opposite end 78 corresponding to waist 34 of balloon/sleeve assembly 14.

Positioned between layers 70 and 72 adjacent to end 78 of layer 72 is a guide tube 80, which facilitates insertion of the temperature sensor array 18 into the balloon portion 26. Guide tube 80 is formed of a flexible polymer, such a Fluorinated Ethylene Plastic or Fluorinated Ethylene Propylene and is skived along a portion of the tube wall facing layer 70 to minimize the amount of material of balloon portion 26 that gets positioned within a patient, i.e., for patient comfort. Opposing edge portions 82 of guide tube 80 are secured to the peripheral edge regions of layers 70 and 72 to hold guide tube 80 in place. End 78 of layer 72 is left unconnected relative to layer 70, such that guide tube 80 separates layers 70 and 72 slightly for easy insertion of the temperature sensor array 18. Layers 70 and 72 are further interconnected by heat welding along seal lines 84 which define channel 30 for the temperature sensor array 18.

Positioned between layers 74 and 76 is the inflation tube 36. Inflation tube 36 is oriented with the flat edge portion 52 of key 50 facing layer 76 and the axis of openings 46 perpendicular to the flat edge portion 52 of key 50. Inflation tube 36 is sealingly connected between layers 74 and 76 at the waist 34 and along end 78. Layers 74 and 76 thereby define an inflatable balloon, which when inflated results in layer 74 bearing directly against layer 72 and indirectly against layer 70 to urge the temperature sensor array 18 in close proximity to the wall of the rectum to be monitored. Layer 76 in turn bears against an opposite rectal wall portion to secure the balloon portion 26 in place in the rectum. In a preferred embodiment layers 70, 72, 74 and 76 have a wall thickness of about 0.2 mil (i.e., about 0.002 inches), which provides for good heat transfer across layer 70 to sensors 20 of the temperature sensor array 18.

In an alternate embodiment, balloon/sleeve assembly 14 may comprise only three layers consisting of layers 70, 72 and 76 that are connected in the manner described above. In such an embodiment, layers 70 and 72 are secured together about the perimeter and guide tube 80 is secured therebetween as previously described. Layers 70 and 72 are then heat sealed along seal lines 84 to form channel 30. Thereafter, inflation tube is positioned between layers 76 and 72 and secured by sealing layer 76 to layer 72 about the perimeter and by sealing the side of layer 72 facing layer 76 to layer 76 along end 78.

In yet another alternate embodiment, layer 72 may be sized and shaped to define channel 30 and sealed about its perimeter to layer 70, with guide tube 80 positioned as previously described between layers 70 and 72. Inflation tube is positioned between layers 70 and 76 and secured by sealing layer 70 to layer 76 about the perimeter and by sealing the side of layer 70 facing layer 76 to layer 76 along end 78.

Figure 6:
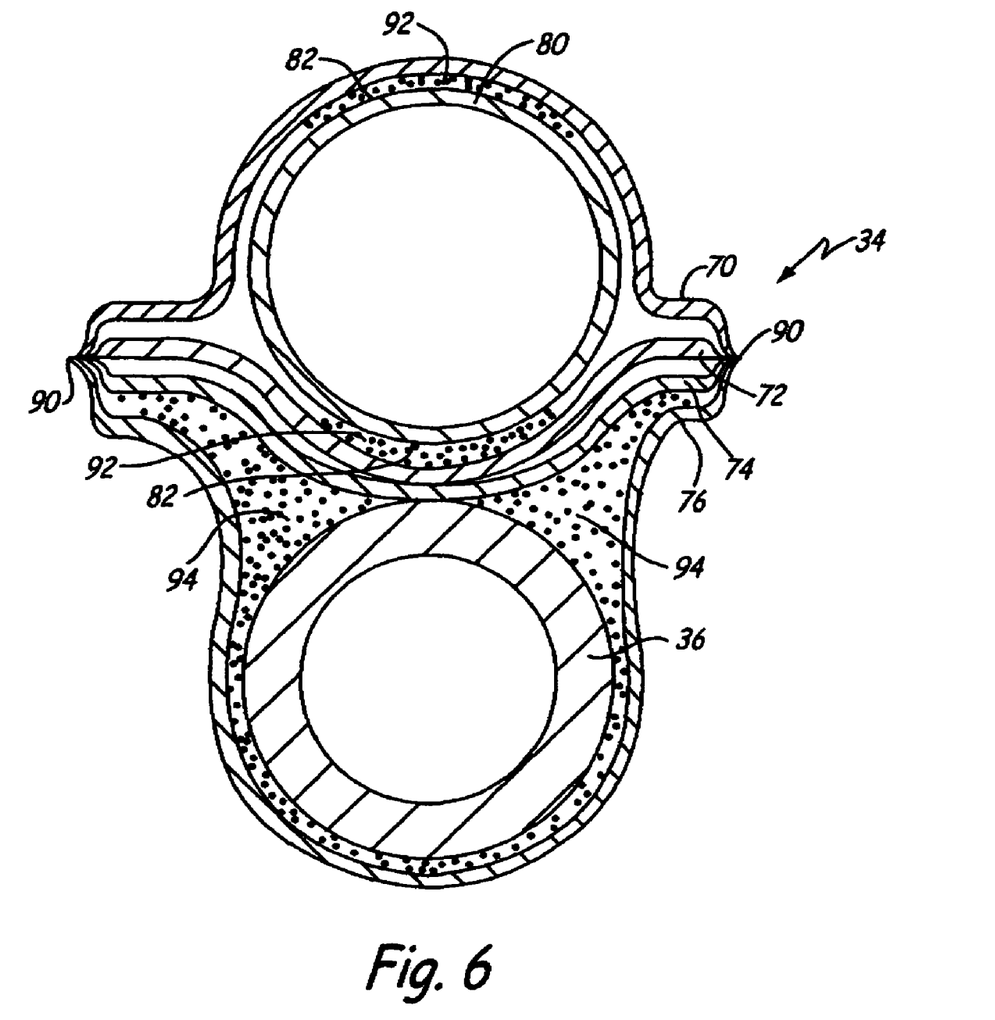
FIG. 6 is a cross-sectional view of the balloon/sleeve assembly of the present invention taken along line 6-6 of FIG. 1.

FIG. 6 is a cross-sectional view of the waist 34 of balloon portion 26, which shows the peripheral heat welds 90 that interconnect peripheral edge portions of layers 70, 72, 74 and 76. FIG. 6 also shows adhesive layers 92, which secure the opposing edge portions 82 of guide tube 80 to layers 70 and 72. Finally, adhesive layer 94 is shown interconnecting end 78 of layer 74 to layer 76 and inflation tube 36 to create a fluid-tight seal at end 78 and thereby form a balloon between layers 74 and 76 that is inflatable and deflatable via the inflation tube 36.

Figure 7:
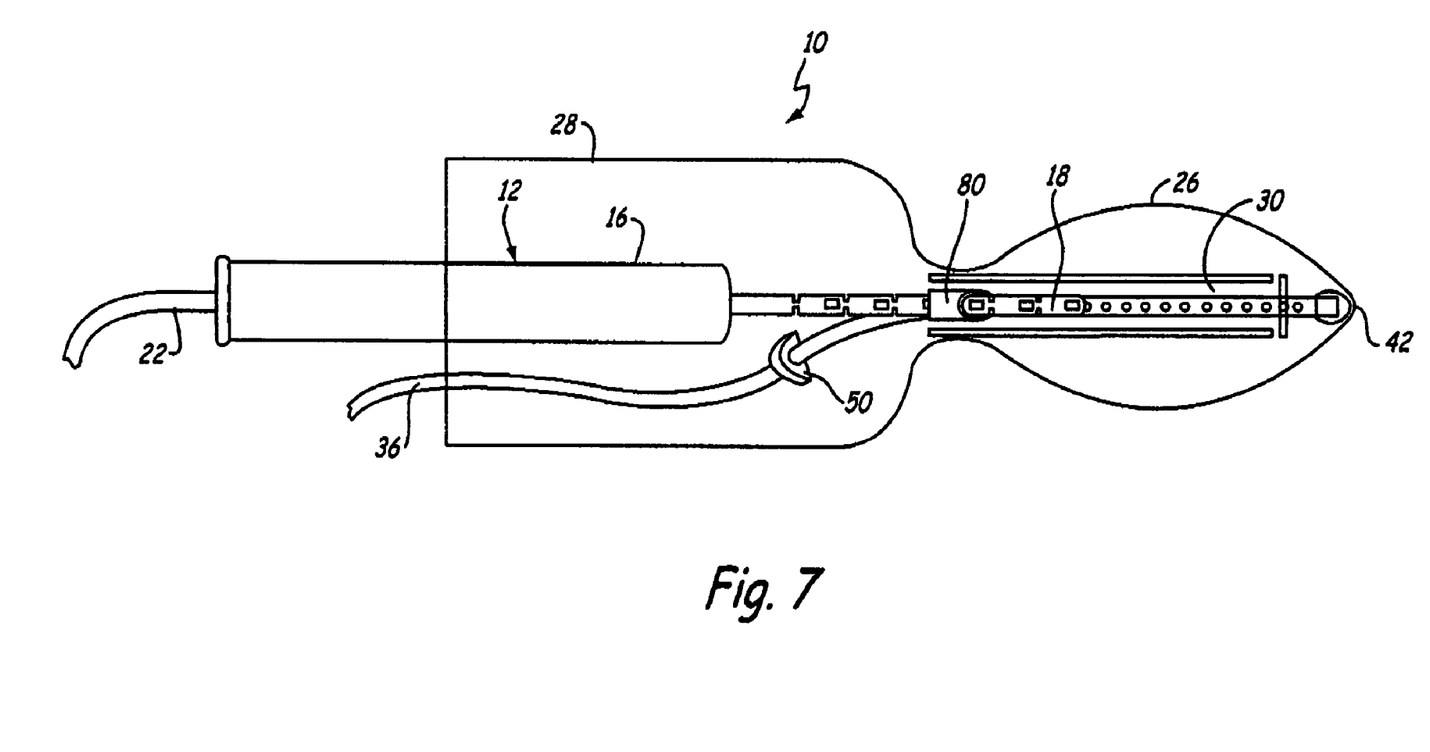
FIG. 7 is a top view of the rectal temperature sensing probe of the present invention with the temperature sensing array partially inserted in a guide tube of the balloon/sleeve assembly.

FIG. 7 is a top view of probe handle 12 being introduced into balloon/sleeve assembly 14 for assembly of rectal temperature sensing probe 10. As shown in FIG. 7, probe handle 12 is inserted through sleeve portion 28 and temperature sensor array 18 is positioned within guide tube 80. Sleeve portion 28 may be folded back over balloon portion 26 to facilitate locating guide tube 80. In one embodiment, guide tube 80 is formed from a distinct color that is readily detectable through the transparent material forming balloon/sleeve assembly 14, which makes the opening for temperature sensor array 18 into channel 30 easy to identify. Probe handle 12 is advanced until temperature sensor array 18 is completely within channel 30, which occurs when key 50 on inflation tube 36 is aligned with the key slot 54 in the handle body 16. Inflation tube 36 is then press fit through opening 48 and into channel 38 along the length of handle body 16 and key 50 is press fit into key slot 54. With sleeve 28 covering handle body 16, temperature sensing probe 10 is then ready for insertion and use in a patient.

Inflation tube 36 is flexible but with sufficient longitudinal stiffness to enable advancement of tip 42 of balloon portion 26 into the desired position within the rectum of a patient. Balloon portion 26 is sized to engage the rectal wall when an inflation medium is introduced via the inflation tube 36 between layers 74 and 76 of the balloon portion 26. With the inflation medium evacuated from the balloon formed by layers 74 and 76, balloon portion 26 reduces to a more compact dimension for easy removal of the balloon portion 26 from the patient. To remove the balloon/sleeve assembly 14 from the probe handle 12, the sleeve portion 28 is everted over balloon portion 26 to isolate the contaminated surface of balloon portion 26. Inflation tube 36 and key 50 are then easily withdrawn from the channel 38 and key slot 58 in the handle body 16. With the inflation tube 36 separated from the handle body 16, probe handle 12 easily slides out of the balloon/sleeve assembly for subsequent re-use with a new balloon/sleeve assembly.

Although the present invention has been described with reference to preferred embodiments, workers skilled in the art will recognize that changes may be made in form and detail without departing from the spirit and scope of the invention.

The invention claimed is:

1. A temperature sensing probe assembly comprising:
   a handle having a length, a width, a first end and a second end;
   a temperature sensor strip carried by the handle and extending from the first end of the handle, the temperature sensor strip comprising a temperature sensor spaced from the first end, the temperature sensor configured for connection to a thermometry device;

a balloon-and-sleeve assembly comprising:

opposing first and second layers of a flexible polymeric material configured to define a balloon and a sleeve that extends longitudinally from the balloon, the balloon further comprising a first interior space in communication with an interior space of the sleeve, and a second interior space isolated from the first interior space and from the interior space of the sleeve; and an inflation tube having a first tube portion sealingly connected within the second interior space of the balloon, the first tube portion configured with an inflation port, the inflation tube further having a second tube portion extending through the interior space of the sleeve and being configured for connection to a fluid source; and wherein the handle is reversibly positionable within the sleeve and the temperature sensor strip is reversibly positionable within the first interior space of the balloon.

2. The temperature sensing probe assembly of claim 1 wherein the balloon comprises a third polymeric layer having a perimeter edge corresponding to a perimeter of the balloon and an end portion facing the sleeve, the perimeter edge connected to the first and second polymeric layers of the balloon, the first and third polymeric layers defining the first interior space of the balloon and the second and third polymeric layers defining the second interior space of the balloon.

3. The temperature sensing probe assembly of claim 2 wherein the first and third layers of the balloon are configured to define a temperature sensor channel, the temperature sensor channel in communication with the interior space of the sleeve.

4. The temperature sensing probe assembly of claim 3 wherein the balloon comprises a waist at a point of transition from the balloon to the sleeve, wherein the first interior space of the balloon comprises an opening defined by an unconnected portion of each of the first and third polymeric layers corresponding to the waist of the balloon, and wherein the opening comprises a guide tube connected to the first and third polymeric layers.

5. The temperature sensing probe assembly of claim 1 wherein the handle further comprises a channel extending along the length of the handle and an opening in a surface of the handle for access to the channel, the channel having an inner diameter that approximates an outer diameter of the second tube portion to receive and removably retain a length of the second tube portion, wherein the opening has a width less than a width of the channel.

6. The temperature sensing probe assembly of claim 5 wherein the handle comprises a curved upper surface and a planar lower surface, the opening being in the flat lower surface.

7. The temperature sensing probe assembly of claim 6 wherein the handle further comprises a key slot in the surface of the handle and wherein the inflation tube further comprises a key on the second tube portion having a configuration complimentary to the key slot, the key being mateable with the key slot when the temperature sensor strip is properly located in the first interior space and the second tube portion is positioned in the channel.

8. The temperature sensing probe assembly of claim 7 wherein the key slot is in the lower surface of the handle.

9. A temperature sensing probe assembly comprising:

a handle having a length, a width, a first end and a second end;

a temperature sensor strip carried by the handle and extending from the first end of the handle, the temperature sensor strip comprising a temperature sensor spaced from the first end, the temperature sensor configured for connection to a thermometry device;

a balloon-and-sleeve assembly comprising:

opposing first and second layers of a flexible polymeric material configured to define a balloon and a sleeve that extends longitudinally from the balloon, the balloon further comprising a first interior space in communication with an interior space of the sleeve, and a second interior space isolated from the first interior space and from the interior space of the sleeve, wherein the balloon comprises a third polymeric layer having a perimeter edge corresponding to a perimeter of the balloon and an end portion facing the sleeve, the perimeter edge connected to the first and second polymeric layers of the balloon, the first and third polymeric layers defining the first interior space of the balloon and the second and third polymeric layers defining the second interior space of the balloon, wherein the first and third layers of the balloon are configured to define a temperature sensor channel, the temperature sensor channel in communication with the interior space of the sleeve, and wherein the temperature sensor channel is defined by first and second spaced heat seal lines connecting opposing surfaces of the first and third layers, the temperature sensor channel being centrally positioned on the balloon; and an inflation tube having a first tube portion sealingly connected within the second interior space of the balloon, the first tube portion configured with an inflation port, the inflation tube further having a second tube portion extending through the interior space of the sleeve and being configured for connection to a fluid source, wherein the handle is reversibly positionable within the sleeve and the temperature sensor strip is reversibly positionable within the first interior space of the balloon.

10. A temperature sensing probe assembly comprising:

a handle having a length, a width, a first end and a second end;

a temperature sensor strip carried by the handle and extending from the first end of the handle, the temperature sensor strip comprising a temperature sensor spaced from the first end, the temperature sensor configured for connection to a thermometry device;

a balloon-and-sleeve assembly comprising:

opposing first and second layers of a flexible polymeric material to define a balloon and a sleeve that extends longitudinally from the balloon, the balloon further comprising a first interior space in communication with an interior space of the sleeve, and a second interior space isolated from the first interior space and from the interior space of the sleeve, wherein the balloon comprises third and fourth polymeric layers each having a perimeter edge connected to the first and second polymeric layers, the first and third layers defining the first interior space of the balloon and the second and fourth layers defining the second interior space of the balloon; and an inflation tube having a first tube portion sealingly connected within the second interior space of the balloon, the first tube portion configured with an inflation port, the inflation tube further having a second tube portion extending through the interior space of the sleeve and movable within the interior space of the sleeve independent of the respective layers defining the sleeve, wherein the second tube portion is configured for connection to a fluid source, wherein the handle is reversibly positionable within the sleeve and the temperature sensor strip is reversibly positionable within the first interior space of the balloon.

11. A balloon-and-sleeve assembly for use with a temperature sensing probe comprised of a handle and a temperature sensor strip extending from one end of the handle, the balloon-and-sleeve assembly comprising:

opposing first and second polymeric layers configured to define a balloon and a sleeve that extends longitudinally from the balloon, the balloon comprising a first enclosed interior space and a second enclosed interior space, the first interior space in communication with an interior space of the sleeve and configured to contain the temperature sensor strip when the handle is positioned in the interior space of the sleeve, the second interior space isolated from the first interior space and the interior space of the sleeve; and an inflation tube having a first tube portion sealingly connected within the second interior space of the balloon, the first tube portion configured with an inflation port, the inflation tube further having a second tube portion extending through the interior space of the sleeve and being configured for connection to a fluid source.

12. The balloon-and-sleeve assembly of claim 11 wherein the sleeve has a length sufficient to cover the handle when the temperature sensor strip is positioned in the first interior space.

13. The balloon-and-sleeve assembly of claim 11 wherein the balloon comprises a third polymeric layer having a perimeter edge corresponding to a perimeter of the balloon and an end portion facing the sleeve, the perimeter edge connected to the first and second polymeric layers of the balloon, the first and third polymeric layers defining the first interior space of the balloon and the second and third polymeric layers defining the second interior space of the balloon.

14. The balloon-and-sleeve assembly of claim 13 wherein the inflation tube is secured between facing surface portions of the second and third polymeric layers.

15. The balloon-and-sleeve assembly of claim 13 and further comprising a guide tube positioned between the first and third layers adjacent to the end portion of the third polymeric layer, the guide tube secured to facing portions of the first and third polymeric layers, the guide tube facilitating insertion of the temperature sensor strip between the first and third polymeric layers and into the first interior space.

16. The balloon-and-sleeve assembly of claim 11 wherein the balloon comprises third and fourth polymeric layers having a perimeter edge connected to the first and second polymeric layers, the first and third layers defining the first interior space of the balloon and the second and fourth layers defining the second interior space of the balloon.

17. The balloon-and-sleeve assembly of claim 16 wherein the inflation tube is secured between facing surface portions of the second and fourth polymeric layers.

18. A balloon-and-sleeve assembly for use with a temperature sensing probe comprised of a handle and a temperature sensor strip extending from one end of the handle, the balloon-and-sleeve assembly comprising:

opposing first and second polymeric layers configured to define a balloon and a sleeve that extends longitudinally from the balloon, the balloon comprising a first enclosed interior space and a second enclosed interior space, the first interior space in communication with an interior space of the sleeve and configured to contain the temperature sensor strip when the handle is positioned in the interior space of the sleeve, the second interior space isolated from the first interior space and from the interior space of the sleeve, wherein the balloon comprises a third polymeric layer having a perimeter edge corresponding to a perimeter of the balloon and an end portion facing the sleeve, the perimeter edge portion connected to the first and second polymeric layers of the balloon, the first and third polymeric layers defining the first interior space of the balloon and the second and third polymeric layers defining the second interior space of the balloon, wherein the balloon further comprises a central channel formed in the first interior space, the central channel comprising spaced first and second seal lines connecting facing surfaces of the first and third polymeric layers, the central channel in communication with the interior of the sleeve for receiving and locating the temperature sensor strip in the first interior space of the balloon; and an inflation tube having a first tube portion sealingly connected within the second interior space of the balloon, the first tube portion configured with an inflation port, the inflation tube further having a second tube portion extending through the interior space of the sleeve and being configured for connection to a fluid source.

* * * * *